(12) United States Patent
Sakamoto et al.

(10) Patent No.: US 8,704,000 B2
(45) Date of Patent: Apr. 22, 2014

(54) METHOD FOR CRYSTALLIZING (METH)ACRYLIC ACID AND METHOD FOR REGULATING CONTENT OF POLYMERIZATION INHIBITOR IN PRODUCT (METH)ACRYLIC ACID

(75) Inventors: Kazuhiko Sakamoto, Himeji (JP); Koji Ueno, Himeji (JP); Yoshitake Ishii, Himeji (JP); Harunori Hirao, Himeji (JP); Satoshi Nakagawa, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 13/322,633

(22) PCT Filed: May 27, 2010

(86) PCT No.: PCT/JP2010/058997
§ 371 (c)(1),
(2), (4) Date: Nov. 28, 2011

(87) PCT Pub. No.: WO2010/140530
PCT Pub. Date: Dec. 9, 2010

(65) Prior Publication Data
US 2012/0071620 A1 Mar. 22, 2012

(30) Foreign Application Priority Data
Jun. 1, 2009 (JP) ................. 2009-132000

(51) Int. Cl.
*C07C 51/43* (2006.01)
*C07C 51/50* (2006.01)

(52) U.S. Cl.
USPC .......................... 562/600; 562/598; 526/317.1

(58) Field of Classification Search
USPC ........................................................ 562/600
See application file for complete search history.

(56) References Cited

U.S. PATENT DOCUMENTS

| | | | |
|---|---|---|---|
| 3,621,664 A | 11/1971 | Saxer | |
| RE32,241 E | 9/1986 | Saxer | |
| 5,504,247 A * | 4/1996 | Saxer et al. | 562/600 |
| 5,935,534 A * | 8/1999 | Umino et al. | 422/245.1 |
| 6,596,901 B1 | 7/2003 | Eck et al. | |

FOREIGN PATENT DOCUMENTS

| | | |
|---|---|---|
| JP | 53041637 B | 11/1978 |
| JP | 09155101 A | 6/1997 |
| JP | 2000514077 A | 10/2000 |

OTHER PUBLICATIONS

Corresponding Chinese Patent Application No. 2010800241525, First Notice of Reasons for Rejection, Jul. 2, 2013.

* cited by examiner

*Primary Examiner* — Vu A Nguyen
(74) *Attorney, Agent, or Firm* — Porzio, Bromberg & Newman, P.C.

(57) ABSTRACT

PROBLEM
There is provided a melting method of (meth)acrylic acid crystal which is capable of providing a higher quality of (meth)acrylic acid without carrying out an additional purification treatment to (meth)acrylic acid obtained by a crystallization operation accompanied by melting of (meth)acrylic acid. In addition, there is provided a simple method for adjusting a content of polymerization inhibitor in a product (meth) acrylic acid.
SOLUTION
In the crystallization method melting (meth)acrylic acid crystal while wetting with the crystalline molten liquid, a polymerization inhibitor is added to a molten liquid melted after initiation of melting, and all of crystal is melted while circulating and feeding the molten liquid containing said polymerization inhibitor to the crystal. In addition, a content of polymerization inhibitor in product (meth)acrylic acid is adjusted by adding a predetermined amount of polymerization inhibitor corresponding to a product specification to the molten liquid melted after initiation of melting.

8 Claims, 3 Drawing Sheets

METHOD FOR CRYSTALLIZING (METH)ACRYLIC ACID AND METHOD FOR REGULATING CONTENT OF POLYMERIZATION INHIBITOR IN PRODUCT (METH)ACRYLIC ACID

CROSS REFERENCE TO RELATED APPLICATION

This is a National Stage of International Application No. PCT/JP2010/058997, filed May 27, 2010, which claims the benefit of Application No. 2009-132000, filed in Japan on Jun. 1, 2009, the disclosures of which Applications are incorporated by reference herein.

TECHNICAL FIELD

The present invention relates to a method for crystallizing (meth)acrylic acid (hereinafter, also simply referred to as "acrylic acid"). In more detail, the present invention relates to a method for crystallizing acrylic acid particularly suitably used for melting of acrylic acid crystal in the crystallization step of cycle (in the present invention, this cycle is referred to as "acrylic acid production cycle") for producing an acrylic acid through a catalytic gas phase oxidation step, collection and/or condensation step, as well as distillation purification and/or crystallization step. In addition, the present invention relates to a method for adjusting a content of polymerization inhibitor in a product acrylic acid. It should be noted that in the present description, (meth)acrylic acid means acrylic acid or methacrylic acid.

BACKGROUND ART

Production of acrylic acid by the above-described acrylic acid production cycle has been widely carried out industrially. In the above-described crystallization step, acrylic acid crystal is crystallized by cooling an aqueous acrylic acid solution from the collection and/or condensation step, and this crystal is sweated and then melted to obtain a purified (product) acrylic acid. It is generally well-known that for implementation of this crystallization step, for example, dynamic crystallizer and static crystallizer are used.

For example, Patent Literature 1 (JP-B-53-41637; U.S. Pat. No. 3,621,664 corresponding to this) describes a technique where one component in a liquid mixture is sequentially concentrated by a multistep fractional crystallization method and fractionated. It has been described that in the multistep crystallization cycle, a purified molten liquid is obtained by melting the crystal obtained in a crystallization operation in a purification stage carried out in the cycle just before the cycle where crystallization step is implemented, and the purified molten liquid is heated and fed to the crystal to melt the relevant crystal.

In addition, Patent Literature 2 (JP-A-155101, U.S. Pat. No. 5,935,534 corresponding to this) describes a crystallization method where a polymerization inhibitor is added to a purified molten liquid having an equivalent purity to the crystallized crystal, and at a same time, this molten liquid is heated up to a temperature of the freezing point of the crystal or higher and circulated and fed to the crystal, to melt the relevant crystal, and the molten liquid is recovered together with the purified molten liquid added a polymerization inhibitor. As the purified molten liquid having an equivalent purity to the crystallized crystal to which polymerization inhibitor is added, use of the purified molten liquid obtained by melting the crystal obtained in a crystallization operation in a purification stage implemented in the cycle just before the cycle where crystallization step is implemented, has been described. In addition, a method where, when crystallization operation is repeated in a multistage, crystal is melted by adding a crystalline molten liquid of the same purification stage to a crystal in the same stage of another cycle, has been also described. In this literature, in order to add a polymerization inhibitor, a storage tank to store the crystalline molten liquid for the aforementioned purpose must be necessarily installed. In addition, a means to heat the crystalline molten liquid is also required.

PRIOR ART LITERATURES

Patent Literature

Patent Literature 1: JP-B-53-41637 (U.S. Pat. No. 3,621,664)
Patent Literature 2: JP-A-9-155101 (U.S. Pat. No. 5,935,534)

DISCLOSURE OF INVENTION

Problem to be Solved by the Invention

By the method described in the Patent Literature 2, acrylic acid having a sufficiently high quality could not be obtained at low cost in an industrial implementation.

Therefore, it is an object of the present invention to provide a crystallization method of acrylic acid which is capable of markedly improving quality of acrylic acid at a low cost.

It is another object of the present invention to provide a simple adjustment method of a content of polymerization inhibitor in a product acrylic acid which has been purified by the crystallization method.

Means for Solving the Problem

According to the study by the present inventors, it has been found that when acrylic acid crystal is melted under the specified conditions, that is, when crystal is melted while wetting the crystal with a molten liquid after initiation of melting, the object can be achieved by adding a polymerization inhibitor (in the present description, "polymerization inhibitor" is sometimes referred to as "stabilizer") in a form of solid or concentrated solution, or the like directly to said molten liquid itself generated in the same cycle and same stage, without installing an exclusive molten liquid tank or heating means for molten liquid at melting of crystal. Based on this knowledge, the present invention was completed.

That is, the present invention is a method for crystallizing acrylic acid by melting acrylic acid crystal while wetting with crystalline molten liquid, characterized in that a polymerization inhibitor is added to a molten liquid melted after initiation of melting, and all of crystal is melted while circulating and feeding the molten liquid containing said polymerization inhibitor to the crystal.

In addition, another aspect of the present invention is a method for adjusting a content of polymerization inhibitor in product acrylic acid, characterized by comprising: melting acrylic acid crystal in the final purification stage of multistep crystallization operation; adding a predetermined amount of polymerization inhibitor corresponding to a product specification to a molten liquid melted after initiation of melting; melting all of crystal while circulating and feeding the molten liquid containing said polymerization inhibitor to the crystal; and thereafter taking out as a product acrylic acid to outside the system.

Effect of the Invention

According to the present invention, a crystallization method for acrylic acid which is capable of remarkably improving quality of acrylic acid at a low cost can be provided.

According to the present invention, a simple adjustment method for a content of polymerization inhibitor in a product acrylic acid which has been purified by the crystallization method can be provided.

According to the method of the present invention, acrylic acid having a sufficiently high quality can be obtained at low cost without carrying out an additional purification treatment to acrylic acid which is obtained by crystallization operation accompanied by melting of acrylic acid crystal. That is, this method is the one obtained by adding a polymerization inhibitor to a part of a molten liquid of final product, and circulating the molten liquid. Therefore, the molten liquid obtained by this method can be used as a final product as it is. For this reason, no additional purification treatment is required. Thus, concentration of the polymerization inhibitor can be easily adjusted to a product specification, by adding a polymerization inhibitor to a molten liquid of acrylic acid in the final step of production.

EMBODIMENTS FOR CARRYING OUT THE INVENTION

Figure 1:
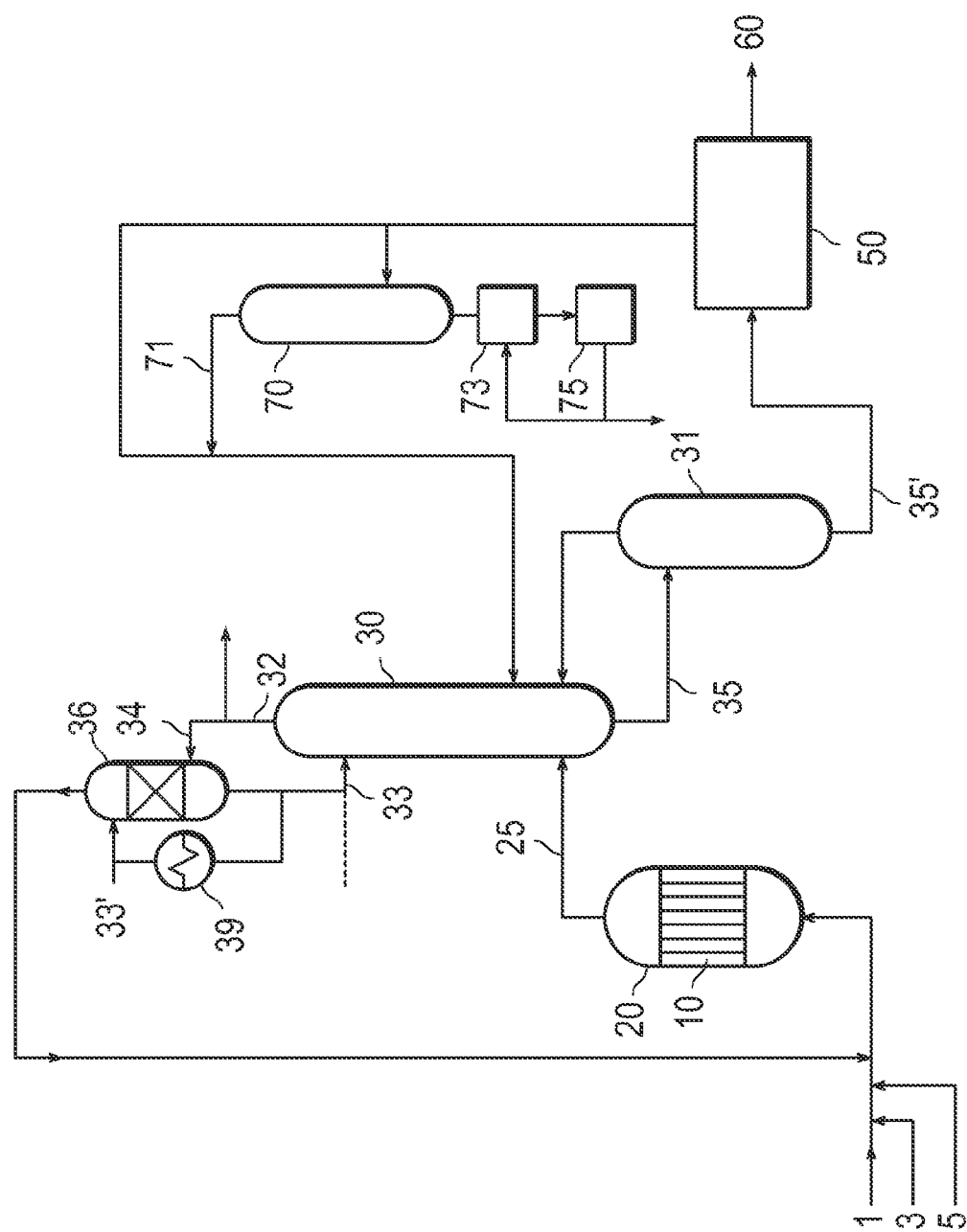
FIG. 1 is a process chart illustrating one example of production method for acrylic acid to obtain a crude acrylic acid to which the crystallization method of the present invention is applied.

The first aspect of the present invention is a method for crystallizing acrylic acid by melting acrylic acid crystal while wetting with crystalline molten liquid, wherein a polymerization inhibitor is added to a molten liquid melted after initiation of melting, and all of crystal is melted while circulating and feeding the molten liquid containing said polymerization inhibitor to the crystal. This crystallization method is also referred to as the "crystallization of the present invention".

In addition, the second aspect of the present invention is a method for adjusting a content of polymerization inhibitor in product acrylic acid comprising: melting acrylic acid crystal in the final purification stage of multistep crystallization operation; adding a predetermined amount of polymerization inhibitor corresponding to a product specification to a molten liquid melted after initiation of melting; melting all of crystal while circulating and feeding the molten liquid containing said polymerization inhibitor to the crystal; and thereafter taking out as a product acrylic acid to outside the system.

The method for producing acrylic acid is not particularly limited, and conventionally known knowledge can be applied by appropriately referring to or combining them. For example, an acrylic acid solution can be obtained by subjecting at least one kind of raw material of acrylic acid selected from a group consisting of alkane, alkene, alkanol and alkanal having 3 to 4 carbon atoms, specifically, propane, isobutene, propylene, isobutylene, acrolein, methacrolein, t-butanol, isobutylaldehyde or methyl t-butyl ether to catalytic gas phase oxidation reaction in the presence of molecular oxygen and conventionally known catalyst to obtain a reaction gas, and bringing such reaction gas into contact with an aqueous solution for collection (such step is also referred to as "acrylic acid collection step"). Thus, acrylic acid is produced, but since such acrylic acid solution usually contains impurities, purification operation is carried out in order to remove these impurities as much as possible. Such purification operation includes various operations such as distillation operation, diffusion operation, crystallization operation and extraction operation.

The present invention is characterized by crystallization operation among such purification operations. Therefore, the crystallization method of the present invention may be applied directly to an acrylic acid solution, which is obtained by carrying out a conventionally known catalytic gas phase oxidation reaction to obtain a reaction gas, and bringing such reaction gas into contact with an aqueous solution for collection to obtain an acrylic acid solution. That is, the crystallization method for acrylic acid of the present invention is preferably used as one of purification operations when acrylic acid is produced. In other words, in the production method for acrylic acid of the present invention, as far as the crystallization method of the present invention is used, conventionally known techniques can be applied by appropriately referring to or combining them in the rest.

Hereinafter, a preferred embodiment of production method for acrylic acid using the crystallization method of the present invention will be explained by means of FIG. 1.

Firstly, a gas containing molecular oxygen such as air 3, raw material of acrylic acid 1 such as propylene and/or acrolein and dilution gas 5 are mixed. After passing through the acrylic acid collection step, recycle gas 34 which is discharged from the top of collection tower can also be mixed with air, propylene and/or acrolein and dilution gas. This mixed gas (hereinafter, also referred to as "raw material gas") is fed to reactor 20 which is packed with catalytic gas phase oxidation catalyst 10, to obtain acrylic acid containing gas 25 by a catalytic gas phase oxidation reaction.

Said gas 25 is fed to the bottom of the collection tower 30, and aqueous solution for collection 33 is fed from the top of said collection tower 30, to bring acrylic acid containing gas 25 and aqueous solution for collection 33 into contact. To said collection tower 30, preferably distillate 71 from distillation tower 70 described later and at least a part of residual mother liquid from crystallizer 50 described later are fed.

It should be noted that the residual mother liquid in the first stage is preferably returned to collection tower 30 after removing high-boiling impurities in distillation tower 70, because the mother liquid in the first stage contains a lot of impurities.

Out of discharge gases 32 from the top of collection tower 30, only recycle gas 34 is introduced into cooling tower 36, and cooled by gas-liquid contact with water for collection 33' which is newly fed into the system, to condensate condensable substances contained in recycle gas 34, and remaining uncondensed gas is circulated to reactor 20. The condensate may be mixed with water for collection 33' and fed to collection tower 30 as aqueous solution for collection 33. It should be noted that in the present description, out of discharge gases 32 from the top of collection tower 30, the discharge gas to be circulated to the reactor is referred to as "recycle gas", and the discharge gas to be discharged off to outside the system is referred to as "waste gas". In such way, in the preferred embodiment of the production method for acrylic acid of the present invention, acrylic acid containing solution 35 containing a high concentration of acrylic acid can be obtained from the bottom of the collection tower, by circulating distillate from distillation tower 71 and cooling recycle gas 34. In the present invention, the crystallization method of the present invention may be applied to such acrylic acid containing solution 35. The crystallization method of the present invention may also be applied to acrylic acid containing solution 35 which is obtained by feeding said gas 25 to the bottom of collection tower 30, and feeding aqueous solution for collection 33 from the top of said collection tower 30 to bring acrylic acid containing gas 25 and aqueous solution for collection 33 into contact, without carrying out the operation that uncondensed gas is circulated to reactor 20.

On the other hand, acrylic acid containing solution 35 may sometimes contain acrolein. Therefore, in a preferred embodiment of the production method for acrylic acid of the present invention, acrylic acid containing solution 35' containing a reduced amount of acrolein is obtained from the bottom of tower, by feeding acrylic acid containing solution 35 to acrolein separation tower 31 to separate the contained acrolein (acrolein separation step). It should be noted that the distillate from the top of separation tower 31 is preferably circulated to the bottom of collection tower 30, because acrylic acid distilled out together with acrolein can be effectively recovered.

Subsequently, product acrylic acid 60 can be obtained by feeding said acrylic acid containing solution 35' to crystallizer 50. The crystallization method in the production method for acrylic acid of the present invention is a characteristic part of the present invention, and will be explained later in detail.

On the other hand, as described above, preferably at least a part of residual mother liquid from crystallizer 50 is fed to the middle stage of distillation tower 70 to distill the contained low-boiling substances and acrylic acid from the top of tower (acrylic acid containing solution distillation step), and said distillate 71 is circulated to the collection tower 30.

In addition, since acrylic acid dimer is contained in a high-boiling substances contained in the bottom liquid of distillation tower 70, preferably this dimer is thermally decomposed to acrylic acid by maintaining the bottom liquid in thermal decomposition tank 75 through thin-film evaporator 73 (acrylic acid dimer decomposition step). Waste oil loss can be recovered by returning this acrylic acid to thin-film evaporator 73, and then distilling from the top of distillation tower 70 to distillate 71, which is circulated to collection tower 30.

The present invention is characterized in that the crystallization method of the present invention is applied to the acrylic acid containing solution obtained by collecting with an aqueous solution as it is, as described above, or after reducing acrolein by an acrolein separation treatment, or to the acrylic acid containing solution obtained by circulating the acrylic acid containing solution after removing a high-boiling substance by distillation or after converting the high-boiling substance to acrylic acid.

Content of acrylic acid in the acrylic acid containing solution in this case is preferably 80% by mass or more, more preferably 85% by mass or more, and further more preferably 87% by mass or more. Content of acrylic acid is preferably 80% by mass, from the viewpoint to avoid the process becoming cumbersome due to increased number of crystallization operations which are carried out to obtain acrylic acid crystal by the crystallizing treatment.

It should be noted that since the present description is characterized by the crystallization step, as for explanations of other steps, for example, acrylic acid collection step, acrolein separation step, acrylic acid containing solution distillation step, acrylic acid dimer decomposition step, and the like, the disclosures of JP-A-2005-15478 (US-2004-249199-A1, corresponding to this) have been incorporated herein in their entireties.

In addition, the catalytic gas phase oxidation reaction when propylene is used as a raw material is usually carried out in 2 stages, and two kinds of catalytic gas phase oxidation catalysts 10 are used. The catalyst in the first stage is the one which is capable of forming mainly acrolein by a gas phase oxidation of the raw material gas containing propylene, and the catalyst in the second stage is the one which is capable of forming mainly acrylic acid by a gas phase oxidation of the raw material gas containing acrolein. The catalyst in the first stage includes complex oxide containing iron, molybdenum and bismuth, and the catalyst in the second stage includes a catalyst containing vanadium as an essential component.

Further, FIG. 1 illustrates an embodiment where the above-described second stage reaction is carried out by a single reactor, but the reaction may be carried out by a tandem system where two different reactors are connected. Acrylic acid containing gas 25 obtained by the catalytic gas phase oxidation reaction contains 5 to 14% by volume of acrylic acid, 0.1 to 2.5% by volume of acetic acid, 0.5 to 3% by volume of molecular oxygen and 5 to 36% by volume of water, and the rest is unreacted components in the raw material gas and reaction by-product substances such as propionic acid, maleic acid, acetone, acrolein, furfural, formaldehyde and $CO_x$.

In acrylic acid collection tower 30, as a contacting method of the acrylic acid containing gas and the aqueous solution for collection, known contacting method can be used, and includes, for example, cross-flow contact using bubble cap tray, uniflat tray, sieve tray, jet tray, bubble tray and venturi tray; counter-current contact using turbo-grid tray, dual flow tray, ripple tray, Kittel tray, gauze-type, sheet-type, grid-type regular packings and irregular packings; and the like.

According to the preferred embodiment of the production method for acrylic acid of the present invention, when acrylic acid is collected by bringing said acrylic acid containing gas 25 and aqueous solution for collection 33 into contact, preferably distillate 71 from distillation tower 70 described later and residual mother liquid from crystallizer 50 described later (hereinafter, these are referred to as "circulation liquid") are fed to the middle stage of collection tower 30.

The acrylic acid collection tower is generally operated at a normal pressure or higher. In the present invention, tower top pressure (gauge pressure) is preferably 0 to 0.4 MPa, more preferably 0 to 0.1 MPa, and further more preferably 0 to 0.03 MPa. The tower top pressure is preferably 0 MPa (gauge pressure) or higher from the viewpoint to minimize equipment cost and utilities cost without using pressure reducing equipment, and also preferably 0.4 MPa (gauge pressure) or lower from the viewpoint to improve collection efficiency by suppressing an extreme increase of the collection tower temperature to discharge low-boiling substances from the tower top.

In addition, tower top temperature is generally 30 to 85° C., and particularly preferably 40 to 80° C.

In the present invention, under such collection conditions, acrylic acid containing solution 35 containing 80 to 98% by mass of acrylic acid, 1 to 19% by mass of water, and 1 to 10% by mass of other impurities (acids such as acetic acid, maleic acid and propionic acid; aldehydes such as furfural and formaldehyde; and the like) can be obtained.

According to the preferred embodiment of the production method for acrylic acid of the present invention, purified acrylic acid (product acrylic acid) 60 is obtained by feeding acrylic acid containing solution 35 or 35' to crystallizer 50.

In addition, since acrylic acid containing solution 35 or 35' subjected to the acrylic acid collection step is at a high temperature, preferably the solution is cooled down by a heat exchanger or the like, or when the acrylic acid containing solution is temporarily stored in a tank, the solution is cooled down by an external heat exchanger in the tank, and then fed to crystallizer 50. The crystallization method to be used in the present invention is not particularly limited so long as the method is batch system. The crystallization method can be carried out in a single stage or in 2 or more stages. Specifically, the batch system crystallizer and the crystallization method described in JP-A-2005-15478 (US-2004-249199-A1, corresponding to this) can be used. As the batch system crystallizer, for example, layered crystallizer (dynamic crystallizer, manufactured by Sulzer Chemtech Ltd., Switzerland), static crystallizer (manufactured by BEFSPROKEM, France), and the like can be used.

The crystallization method of the present invention is suitably used for an operation to melt an acrylic acid crystal (in particular, to melt by circulating a molten liquid and flowing down like a falling film (Falling Film style)), especially in an acrylic acid crystallization step using a batch system crystallizer. Therefore, here, the present invention will be specifically explained taking a method for melting acrylic acid crystal using a batch system dynamic crystallizer in Falling Film style (for example, the Patent Literature 1) as an example.

Figure 2:
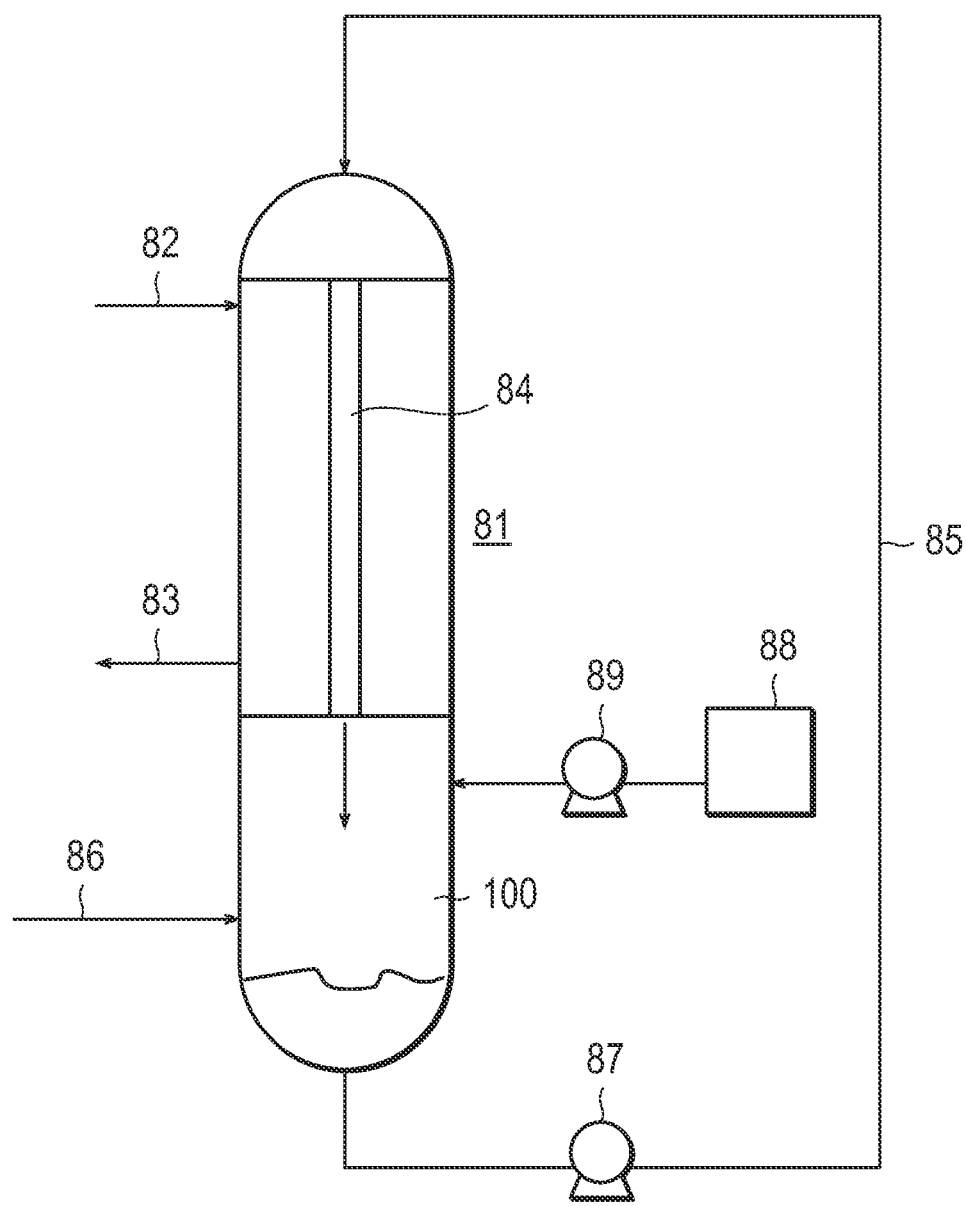
FIG. 2 is an explanatory drawing illustrating one embodiment carrying out the crystallization method of the present invention using a batch system dynamic crystallizer (melt crystallizer).

FIG. 2 is an explanatory drawing illustrating an embodiment of the crystallization method of the present invention using a batch system dynamic crystallizer (melt crystallizer). In crystallizer 50, crystallization tube 84 can be cooled or heated by introducing a cooled or heated medium (temperature of the medium can be adjusted by a thermostat) from line 82 and discharging from line 83, and circulating in the jacket.

(1) Crystallization Operation

In the operation of crystallization (that is, operation to deposit acrylic acid crystal), firstly a cooling medium is circulated in the jacket as described above. On the other hand, in the tube side, acrylic acid containing solution 35 or acrylic acid containing solution 35' is introduced from line 86. After a predetermined amount is introduced, the tube is closed. It should be noted that such predetermined amount depends on a production scale (crystallizer), because amount of crystal to be attached per one crystallization tube is fixed.

Subsequently, by cooling acrylic acid containing solution 35 or acrylic acid containing solution 35' by circulating through line 85, acrylic acid is allowed to crystallize on the inner surface of crystallization tube 84 (that is, acrylic acid crystal is deposited). In this case, the number of the crystallization tube 84 may be multiple, though only one in FIG. 2. Upper limit of the number is not particularly limited, so long as the number does not disturb dispersion of the liquid or does not degrade product quality.

The acrylic acid crystal which is obtained by crystallizing crude acrylic acid (acrylic acid containing solution 35 or acrylic acid containing solution 35') using a dynamic crystallizer described later can have 80% by mass or more of acrylic acid concentration in the acrylic acid containing solution, and therefore can shorten the time of crystallization operation. Thus, such acrylic acid crystal is preferable from the viewpoint of productivity.

In addition, the acrylic acid crystal which is obtained by crystallizing a crude acrylic acid (acrylic acid containing solution 35 or acrylic acid containing solution 35') using a melt crystallizer described later can have 80% by mass or more of acrylic acid concentration in the acrylic acid containing solution, and therefore can shorten the time of crystallization operation. Thus, such acrylic acid crystal is preferable from the viewpoint of productivity.

Amount of the acrylic acid crystal to be deposited is preferably 95 to 50% by mass relative to the total amount of the predetermined amount (an amount of acrylic acid containing solution 35 or acrylic acid containing solution 35' fed during the time from introduced to closed). Temperature of the cooling medium in this case is also not particularly limited, so long as the temperature is the one by which the desired amount can be deposited. It should be noted that the temperature of this cooling medium and the temperature of the inner surface of crystallization tube 84 are regarded as substantially equivalent.

At least a part of the rest of acrylic acid containing solution 35 or acrylic acid containing solution 35' which is not deposited as an acrylic acid crystal is fed to the middle stage of distillation tower 70, as a residual mother liquid from crystallizer 50. After high-boiling impurity is cut off, low-boiling substances and acrylic acid contained therein are distilled from the top of tower, and said distillate 71 is preferably circulated to the collection tower 30. The rest thereof is preferably circulated directly to collection tower 30.

(2) Sweating Operation

Subsequently, sweating of the acrylic acid crystal deposited on the inner surface of crystallization tube 84 is carried out by changing from the cooling medium to a heating medium. It should be noted that "sweating" means a phenomenon or an operation where impurities originated from the mother liquid (that is, acrylic acid containing solution 35 or acrylic acid containing solution 35') which is incorporated in crystal are removed from the crystal by increasing temperature of the crystal or the like. In the crystallization method of the present invention, the sweating can be carried out by melting a part of the acrylic acid crystal deposited as described above.

In this case, temperature of the heating medium to be introduced for melting is also not particularly limited, but preferably is near the melting point of acrylic acid, because at a significantly higher temperature than the melting point, all of crystal melts out and sweating effect is impaired. The impurities are eluted out by melting acrylic acid. On the other hand, when temperature is increased to near the melting point of acrylic acid at once, acrylic acid melts out at once, leading to not partial melting but full melting. Therefore, temperature is preferably gradually increased from a temperature of the melting point or lower.

Out of the acrylic acid crystal deposited as described above, amount of the crystal to be sweated (partially melted) is also not particularly limited, but preferably 0.01 to 30% by mass based on the total amount of the acrylic acid crystal deposited, from the viewpoint to remove impurities effectively. When amount to be sweated is increased, amount of the impurities to be removed increases but acquirable yield of acrylic acid decreases. Therefore, the amount in around the above-described range is preferable.

Impurity of acrylic acid to be produced is improved by carrying out the sweating operation in this way.

(3) Melting Operation

After the above-described sweating operation (after the sweated liquid is discharged to outside the system together with residual mother liquid), the acrylic acid crystal deposited is melted to obtain a molten liquid (also referred to as "crystalline molten liquid").

The crystallization method of the present invention is characterized in that a polymerization inhibitor is added to the molten liquid melted after initiation of the melting, and all of crystal is melted while circulating and feeding the molten liquid containing said polymerization inhibitor to the crystal (the acrylic acid crystal deposited).

The constitution that a polymerization inhibitor is added to the molten liquid melted after initiation of melting means, in other words, that a tank to store the crystalline molten liquid is not necessarily installed. That is, since the molten liquid melted after initiation of the melting is accumulated in the bottom of crystallizer 50, and the polymerization inhibitor can be added thereto, a tank to store the crystalline molten liquid becomes unnecessary. That is, in the present invention, an effect that an equipment configuration for producing acrylic acid is simplified is successfully exhibited. And the molten liquid containing said polymerization inhibitor is circulated and fed to the crystal. Since the crystal is warmed up by utilizing heat from the heating medium flowing outside of the wall of crystallization tube, in other words, while circulating without heating in advance, a separate heating means becomes unnecessary. That is, in the present invention, an effect that an equipment configuration for producing acrylic acid is simplified is successfully exhibited in this point too. That is, the present invention can provide a crystallization method for acrylic acid at low cost. In addition, since it is not necessary to prepare a liquid containing a polymerization inhibitor separately in advance as in the prior art literatures, the method of the present invention is preferable also in the point that the method of the present invention results in improvement in productivity. In addition, when a dilute mother liquid containing a polymerization inhibitor must be prepared, the dilute mother liquid must be heated in advance. The present invention results in reduction in production time, and eventually improvement in productivity, because such heating is not required. In addition, in the present invention, a concentrated solution or a solid can be added directly, quality of product acrylic acid (in particular, from the viewpoint of color) is improved.

Here, "molten liquid melted after initiation of the melting" (also referred to as "initial molten liquid") will be explained. On the inner surface of crystallization tube 84, acrylic acid crystal containing a reduced amount of impurities through the sweating operation has been adhered. Such acrylic acid crystal containing a reduced amount of impurities through the sweating operation is melted by heating with a heating medium. However, all of crystal is not necessarily melted at once by the heating. A part of the acrylic acid crystal containing a reduced amount of impurities through the sweating operation which is adhered on the inner surface of crystallization tube 84 is melted, and the "molten liquid melted after initiation of the melting" means the molten liquids melted from a part of the crystal. It should be noted that the polymerization inhibitor may be added before melting in advance, so long as the polymerization inhibitor can be added to the molten liquid melted. Since a certain amount of the molten liquid is required for pump circulation, timing of addition of the polymerization inhibitor may be from "before the molten liquid starts to melt (the polymerization inhibitor may be added before molten liquid is accumulated in advance) to "when a minimum amount for pump circulation of the molten liquid is accumulated".

The crystallization method of the present invention is characterizes in that the polymerization inhibitor is added to such the "molten liquid melted after initiation of the melting". And, the crystallization method of the present invention is also characterizes in that all of acrylic acid crystal adhered on the inner surface of crystallization tube 84 is melted by circulating and feeding the molten liquid containing said polymerization inhibitor to the acrylic acid crystal containing a reduced amount of impurities through the sweating operation which is adhered on the inner surface of crystallization tube 84, and wetting on such acrylic acid crystal. In more simply, the crystallization method of the present invention is characterized in that all of crystal is melted by adding the polymerization inhibitor to the initial molten liquid from the main body of acrylic acid crystal containing a reduced amount of impurities through the sweating operation, and circulating them.

The molten liquid melted after initiation of the melting is accumulated in collector section 100 in the bottom of the crystallizer. The polymerization inhibitor is preferably added to the molten liquid melted after initiation of the melting accumulated in this collector section 100. In other words, the polymerization inhibitor is preferably added directly to the collector section of said crystallizer. This procedure is preferable because a molten liquid containing the polymerization inhibitor can be easily prepared.

And, all of crystal is melted while circulating and feeding the molten liquid containing said polymerization inhibitor to the crystal. Conditions for adding the polymerization inhibitor to the molten liquid melted after initiation of the melting is not particularly limited, but it is particularly preferable to add the polymerization inhibitor in a form of solid or concentrated solution to the molten liquid melted after initiation of the melting. When the polymerization inhibitor in a concentrated solution is added, said concentrated solution may be charged into tank 88, and introduced into collector section 100 by pump 89. In this case, amount of the solid or the concentrated solution to be added is also not particularly limited, so long as a concentration of acrylic acid taken out as a product complies with product specification. Thereby, circulated molten liquid flows down while wetting the acrylic acid crystal to facilitate melting of the acrylic acid crystal. In addition, when the polymerization inhibitor in solid form is added, the polymerization inhibitor may be added to collector section 100 using an automatic feeder instead of tank 88 and pump 89, or the polymerization inhibitor may be added manually directly to collector section 100. In this case, amount of the polymerization inhibitor in solid form to be added is also not particularly limited.

The polymerization inhibitor is appropriately selected from the conventionally known inhibitors to be used. Specifically, there may be used one or more kinds of compounds selected from a group consisting of N-oxyl compound such as 2,2,6,6-tetramethylpiperidino-1-oxyl; phenol compound such as p-methoxyphenol; manganese salt compound such as manganese acetate; copper dialkyldithiocarbamate salt compound such as copper dibutylditiocarbamate; nitroso compound; amine compound; and phenothiazine compound. Preferably, there are used one or more kinds of compounds selected from N-oxyl compound such as 2,2,6,6-tetramethylpiperidino-1-oxyl; phenol compound such as p-methoxyphenol; and manganese salt compound such as manganese acetate. Use of the above-described one or more kinds of compounds selected from N-oxyl compound, phenol compound and manganese salt compound is preferable, because acrylic acid having a superior color tone and sufficiently high quality can be obtained.

Here, when the crystallization method of the present invention is implemented using a concentrated polymerization inhibitor solution, the lower limit of the polymerization inhibitor concentration in the concentrated polymerization inhibitor solution (mass of the polymerization inhibitor to the total mass of the mother liquid and the polymerization inhibitor) is preferably 1% by mass or more. A solution of more preferably 2% by mass or more, further more preferably 3% by mass or more, yet further more preferably 4% by mass or more, and particularly preferably 5% by mass or more is used.

It should be noted that, in the collector section in the bottom of the crystallizer, the "molten liquid melted after initiation of the melting" has been accumulated already. Concentration of the polymerization inhibitor in the mother liquid (concentration of the polymerization inhibitor) is preferably adjusted so that a concentration of the polymerization inhibitor in the acrylic acid becomes the concentration set in the specification of product acrylic acid when all of acrylic acid crystal is melted.

On the other hand, when concentration of the polymerization inhibitor is less than 1% by mass, sometimes more volume of mother liquid (that is, a solvent to prepare the polymerization inhibitor) is required. It is not preferable that a large volume of mother liquid is introduced into the crystallizer when the acrylic acid crystal is melted, because color tone deterioration by mother liquid affects more significantly. By using a significantly concentrated solution (concentrated solution) as in the present invention, amount of the polymerization inhibitor to be used can be reduced, and eventually reduction of product loss is also resulted (the similar effect can be obtained in the case where a polymerization inhibitor in a form of solid is added). In addition, use of the significantly concentrated solution (concentrated solution) is also preferable, because a small sized tank 88 to store the concentrated solution can be used and hence unnecessary expansion of production facility for acrylic acid can be suppressed (the case where the polymerization inhibitor in a form of solid is added is preferable, because such facility is unnecessary in the first place). In addition, use of the significantly concentrated solution (concentrated solution) in such way results in improvement in product quality (color tone), because color tone deterioration is not influenced strongly (here again, same thing can be said for the case where the polymerization inhibitor in a form of solid is added). It should be noted that adjustment of concentration of "mother liquid" described above is preferably implemented by using product acrylic acid.

It should be noted that, the upper limit of the concentration is not particularly limited, but it is preferable to consider that there is an upper limit in solubility depending on kinds of polymerization inhibitor and mother liquid to be used. From the relationship between a polymerization inhibitor and a solubility of solvent, the upper limit is preferably 50% by mass or less, more preferably 40% by mass or less, further preferably 30% by mass or less, further more preferably 20% by mass or less, and particularly preferably 10% by mass or less.

In addition, as the mother liquid for the polymerization inhibitor, acrylic acid, water, acetic acid, or the like can be used, but use of product acrylic acid is more preferable, because when water or acetic acid is used, an increased concentration of water or acetic acid in a product could lead to deterioration of quality.

It should be noted that, whichever the form of the polymerization inhibitor to be added is a solid or a concentrated solution, the polymerization inhibitor is preferably added so that the concentration becomes the one set for the product acrylic acid when all of acrylic acid is melted.

Further, a concentrated solution of the polymerization inhibitor is preferably introduced into the crystallizer without heating. When a solution of the polymerization inhibitor is heated, color tone of the mother liquid is deteriorated due to alteration of the polymerization inhibitor or the like, and quality of product acrylic acid to be obtained is deteriorated. In addition, since heating is not carried out, heating facility becomes unnecessary, no heating is preferable on this point too.

In addition, timing of addition of the polymerization inhibitor is also not particularly limited, so long as it is such condition that the polymerization inhibitor can be added to the molten liquid melted after initiation of the melting. Since the molten liquid melted after initiation of the melting accumulates in collector section 100 in the bottom of the crystallizer, the polymerization inhibitor may be added to the accumulated molten liquid. In addition, when the polymerization inhibitor is added to collector section 100 in the bottom of the crystallizer in advance, the polymerization inhibitor can be automatically added to the molten liquid, because the molten liquid melted after initiation of the melting accumulates in collector section 100 in the bottom of the crystallizer. Adding in advance is preferable, because the molten liquid does not contain the polymerization inhibitor and could cause polymerization.

As described above, an initial molten liquid containing polymerization inhibitor is prepared, and all of crystal is melted while circulating and feeding it to the crystal. More specifically, a molten liquid flowed out from crystallization tube 84 (the molten liquid containing polymerization inhibitor) is taken out from the bottom section and circulated to the top section by line 85, and flowed down on the acrylic acid crystal. When a concentrated solution of the polymerization inhibitor is charged as described above, said concentrated solution may be charged into tank 88, and introduced into collector section 100 by pump 89. By this operation, the circulated molten liquid (the molten liquid containing polymerization inhibitor) flowed down while wetting the acrylic acid crystal, and facilitates melting of the acrylic acid crystal. In addition, when polymerization inhibitor in a solid form is added, the polymerization inhibitor may be charged into collector section 100 using an automatic feeder instead of tank 88 and pump 89, or the polymerization inhibitor may be directly charged into collector section 100 in hand work.

Amount of this falling liquid is not particularly limited and can be appropriately selected. Since when liquid level in collector section 100 becomes too low by circulating all of molten liquid, cavitation of pump 87 generates a concern, circulation is initiated after the liquid level gets higher to some extent. After that, the liquid level gradually comes up by melting of the crystal. Preferred cycle until the above step is briefly summarized as follows. Acrylic acid raw material gas is subjected to catalytic gas phase oxidation to obtain an acrylic acid gas. And, the acrylic acid gas is brought into contact with an aqueous solution for collection to obtain an acrylic acid solution. And, the acrylic acid solution is introduced into the crystallizer. After that, through the crystallization operation and the sweating operation, a polymerization inhibitor is added to the molten liquid melted after initiation of the melting in the melting operation, and all of crystal is melted while circulating and feeding the molten liquid containing said polymerization inhibitor to the crystal.

The crystallization method of the present invention is characterized in that a polymerization inhibitor in a form of solid, concentrated solution, or the like is added directly to the molten liquid itself generated during one cycle. In other words, the crystallization method of the present invention is characterized in that a polymerization inhibitor in a form of solid, concentrated solution, or the like is added to the molten liquid (initial molten liquid) which is generated after initiating one cycle by introducing the acrylic acid solution (raw material solution) into the crystallizer. In addition, when the polymerization inhibitor is added in a form of a concentrated solution, the solution (mother liquid) is preferably product acrylic acid.

Respective steps comprise operations (dynamic crystallization) consisting of crystallization, sweating and melting as described above. Carrying out 1 time of this crystallization, sweating and melting is referred to as 1 stage of crystallization operation. As 1 cycle, by introducing an acrylic acid solution (collection solution) (acrylic acid containing solution 35') into the crystallizer (the start of 1 cycle), crystallizing and sweating, and preferably in the later stage, melting all of crystal while circulating and feeding the initial molten liquid, to which the polymerization inhibitor is added, to the crystal, the molten liquid can be obtained as a product (the end of 1 cycle).

Thus, when the acrylic acid crystal is melted under a specified condition, that is, while wetting the crystal with the molten liquid after initiation of melting, the object is achieved by directly adding a polymerization inhibitor in a form of solid or concentrated solution or the like to said molten liquid itself generated in the same cycle (the same stage), without providing a molten liquid storage tank for exclusive use and a heating means for the molten liquid in melting of the crystal.

The crystallization operation of the present invention is not limited to multistage crystallization operation, but it is preferable to pass through multistage crystallization operation where dynamic crystallization is carried out plural times (multistage) is employed, from the viewpoint to produce a highly-pure product acrylic acid. The number of stages is also not particularly limited, but preferably 2 to 6 times, more preferably 3 to 5 times, and further more preferably around 3 to 4 times. It should be noted that 1 cycle of crystallization operation means a step to obtain product acrylic acid by repeating the specified times (around 2 to 6 times) of operations.

The crystallization method of the present invention is characterized in that all of crystal is melted while circulating and feeding the initial molten liquid added with the polymerization inhibitor to the crystal. In the case of this multistage crystallization operation, among such plural stages, the addition of the polymerization inhibitor to the initial molten liquid is sufficient by carrying out at least 1 time. However, for example, when 4 stages of crystallizations are carried out, the addition is preferably carried out in the third stage or the fourth stage where purity of acrylic acid has been raised.

Here, 1 cycle of 4 stages crystallization operations (n=4) will be explained as an example.

Figure 3:
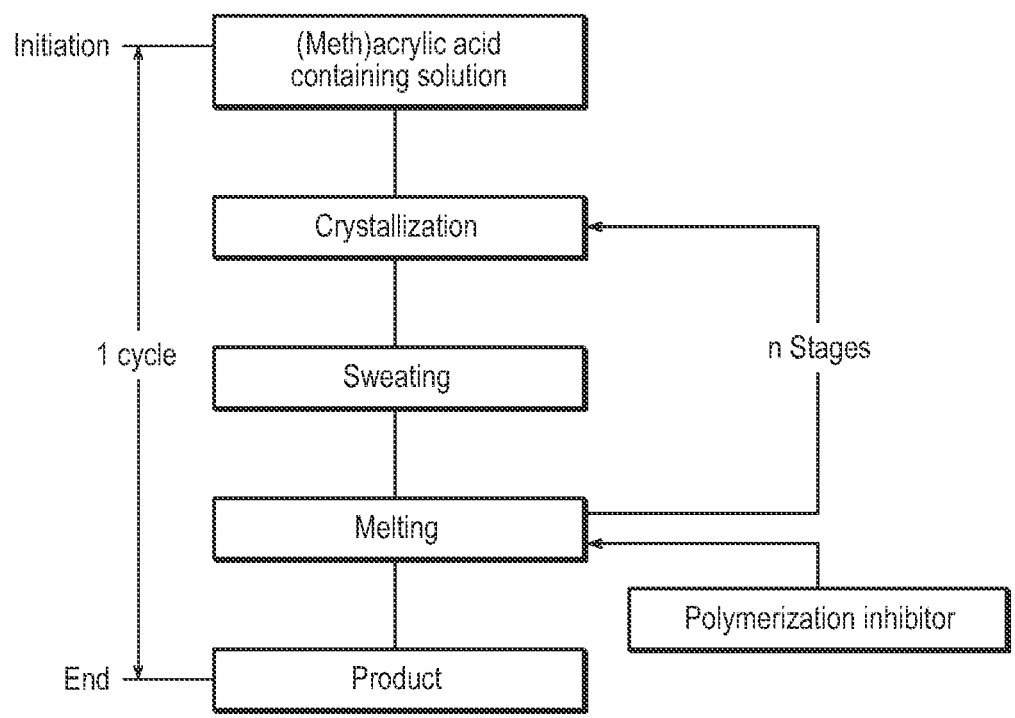
FIG. 3 is a flow chart illustrating steps in a preferable embodiment of the crystallization method of the present invention.

As shown in FIG. 3, an acrylic acid solution is introduced into the crystallizer (the start of 1 cycle). Then, crystallization and sweating are carried out. And, melting is carried out. In this case, the first stage may be terminated by adding a polymerization inhibitor to the initial molten liquid and melting all of crystal while circulating and feeding the initial molten liquid. Subsequently, next is the second stage. The molten liquid obtained in the first stage is introduced into the crystallizer. Then, crystallization and sweating are carried out. And, a polymerization inhibitor may be added to the initial molten liquid in this second stage, and all of crystal may be melted while circulating and feeding the initial molten liquid. Crystallization operations in the third stage and the fourth stage are also the same. However, it is preferable to add the polymerization inhibitor to such initial molten liquid in a later stage than in an earlier stage. For example, in the case of 4-stages crystallization operations, preferably the polymerization inhibitor is added to the initial molten liquid in the third stage and the fourth stage to melt all of crystal. Thus, by controlling the timing of addition of the polymerization inhibitor to the initial molten liquid with gradient, an effect to prevent polymerization of acrylic acid can be obtained. Further, for example, in the case of 1 cycle of 3-stages crystallization operations (n=3), preferably the polymerization inhibitor is added to the initial molten liquid in the second stage and the third stage to melt all of crystal.

Thus, when the acrylic acid crystal is melted under a specified condition, that is, while wetting the crystal with the molten liquid after initiation of the melting, the object is achieved by directly adding a polymerization inhibitor in a form of solid or concentrated solution or the like to said molten liquid itself generated in the same cycle (the same stage), without providing a molten liquid storage tank for exclusive use and a heating means for the molten liquid in melting of the crystal.

It should be noted that, as mentioned above, when this crystallization method of acrylic acid of the present invention is applied to the final purification stage of multistage crystallization operation, the resultant acrylic acid can be taken out to outside the system as a product as it is. In such case, as a polymerization inhibitor to be added to the molten liquid melted after initiation of the melting (initial molten liquid), the polymerization inhibitor specified in the product specification may be selected, and amount to be added may be determined so that the concentration specified in the product specification can be obtained as well, to be added to the molten liquid. By such procedures, an effect that content of the polymerization inhibitor in product acrylic acid can be easily adjusted can be obtained. By the merit that content of the polymerization inhibitor can be easily adjusted, the subsequent step (stabilizer adjustment step) can be simplified and incidental facilities such as tank becomes unnecessary, leading to an effect such as reduction in investment cost.

That is, the second aspect of the present invention is to provide a method for adjusting a content of polymerization inhibitor in product acrylic acid comprising: melting acrylic acid crystal in the final purification stage of multistep crystallization operation; adding a predetermined amount of polymerization inhibitor corresponding to a product specification to a molten liquid melted after initiation of the melting; melting all of crystal while circulating and feeding the molten liquid containing said polymerization inhibitor to the crystal; and thereafter taking out the molten liquid as a product acrylic acid to outside the system.

It should be noted that as for the "polymerization inhibitor specified in the product specification", the specific example of the polymerization inhibitor described above can be applied here as well.

In addition, the "predetermined amount corresponding to a product specification" is not particularly limited, so long as the concentration specified in a product specification can be obtained. In addition, the "concentration specified in a product specification" is preferably 60 to 220 ppm by mass, more preferably 65 to 210 ppm by mass, further more preferably 70 to 210 ppm by mass, and particularly preferably 80 to 205 ppm by mass relative to the total amount of the product acrylic acid.

In order to obtain a concentration in a range of the above described "concentration specified in a product specification", amounts of the polymerization inhibitor (solid) and the concentrated solution to be added may be adjusted by appropriately varying the "predetermined amount corresponding to a product specification" so that the predetermined concentration of stabilizer in a product can be obtained.

It should be noted that, in the present invention, since the added polymerization inhibitor is circulated through collector section 100, pump 87, line 85, and crystallization tube 84 together with acrylic acid, they are homogeneously mixed together. It should be noted that by circulating the liquid for an appropriate time even after melting of the crystal is completed, the polymerization inhibitor can be mixed more homogeneously with respect to the fully-molten acrylic acid.

Acrylic acid (product acrylic acid) obtained by the above-described crystallization method (or adjustment method) can be improved in quality thereof markedly despite of low cost. Purity of acrylic acid in acrylic acid (product acrylic acid) obtained by the above-described crystallization method is preferably 95% by mass or more, more preferably 97% by mass or more, and further more preferably 99% by mass or more.

In addition, color tone (APHA) of acrylic acid (product acrylic acid) obtained by the above-described crystallization method is preferably 20 or less, more preferably 10 or less, and further more preferably 5 or less.

As above-mentioned, the present invention can provide a method for crystallizing acrylic acid which is capable of improving quality of acrylic acid remarkably at a low cost.

In addition, the present invention can provide a method for easily adjusting a content of polymerization inhibitor in product acrylic acid purified by the crystallization method.

In addition, according to the method of the present invention, acrylic acid having a sufficiently high quality can be obtained at low cost without carrying out an additional purification treatment to acrylic acid obtained by the crystallization operation accompanied by melting of the acrylic acid crystal.

It should be noted that in the above-described embodiment, acrylic acid of a raw material is obtained by subjecting propylene to catalytic gas phase oxidation, but as a modified example of the present invention, acrylic acid as a raw material to be used in the crystallization method of the present invention can be obtained by other methods. That is, according to such modified examples, acrylic acid as a raw material to be used in the crystallization method of the present invention may be those obtained by a production method comprising a step where glycerin or 2-methylglycerin is dehydrated to be converted to (meth)acrolein; and a step where such (meth) acrolein is further oxidized to be converted to (meth)acrylic acid, alternatively those obtained by dehydrating hydroxypropionic acid or 2-methyl-3-hydroxypropionic acid to be converted to (meth)acrylic acid. By introducing the resultant (meth)acrylic acid as a raw material through line 86, and subjecting to the crystallization method of the present invention, a purified (meth)acrylic acid is obtained. That is, by introducing crude (meth)acrylic acid obtained by any one of these methods into a crystallizer to be used in the crystallization method of the present invention, and subjecting to the crystallization method of the present invention, a purified (meth)acrylic acid is obtained. It should be noted that since such crystallization method of the present invention is as described in the above item (3) Crystallization step (crystallization method of the present invention), explanation of the method is omitted here.

Hereinafter, a method where glycerin is dehydrated and further oxidized to obtain crude acrylic acid and a method where hydroxypropionic acid (HP) is dehydrated to obtain crude acrylic acid are shown.

<Method for Producing Acrolein by Dehydrating Glycerin>

A method for producing acrolein is the one where glycerin is dehydrated to form acrolein in the presence of a catalyst. The catalyst includes a solid catalyst having an acidic property. The solid acidic catalyst having an acidic property may be a solid compound having an acidic property, and includes (a) crystalline metalosilicate, (b) metal oxide, (c) clay mineral, (d) mineral acid supported on an inorganic carrier such as alumina, silica, zirconium oxide and titanium oxide, (e) metal salt of phosphoric acid and sulfuric acid, and the same supported on an inorganic carrier such as alumina, silica, zirconium oxide and titanium oxide, and the like.

(a) Crystalline metalosilicate is the one containing one or more kinds of elements selected from Al, B, Fe, Ga, and the like as T atoms, and having a crystal structure such as LTA, CHA, FER, MFI, MOR, BEA and MTW. (b) Metal oxide includes, besides a single metal oxide such as $Al_2O_3$, $TiO_2$, $ZrO_2$, $SnO_2$ and $V_2O_5$, a complex oxide such as $SiO_2$—$Al_2O_3$, $SiO_2$—$TiO_2$, $TiO_2$—$WO_3$ and $WO_3$—$ZrO_2$. (c) Clay mineral includes bentonite, kaolin, montmorillonite, and the like. (d) Mineral acid supported on an inorganic carrier includes phosphoric acid and sulfuric acid supported on alumina, silica, zirconia, or the like. (e) As a salt of phosphoric acid or sulfuric acid, there are exemplified $MgSO_4$, $Al_2(SO_4)_3$, $K_2SO_4$, $AlPO_4$, $BPO_4$, $Zr_3(PO_4)_4$, and the like. Specifically, the solid acid (zirconium oxide supporting phosphoric acid, sulfuric acid or tungsten oxide, or the like) which has been disclosed in WO 2006/087083 and WO 2006/087084 can be used. Among them, since the catalyst is exposed to high temperature and oxidative or reductive atmosphere in the dehydration reaction or regeneration treatment, a solid catalyst having superior stability is preferable, and crystalline metalosilicate, metal oxide, clay mineral, and the like are preferable. As a crystalline metalosilicate, HZSM 5 containing Al as a T atom and having MFI structure, as a metal oxide, crystalline phosphate salt compound are preferable. Aluminium phosphate is particularly preferable. HZSM 5 shows strong acidity having peaks at around −9 and −16 in Hammett acidity function HO (Kenji Hashimoto, et al., Shokubai Vol. 29, No. 6, p 406-409, 1987), and acidity of aluminium phosphate varies depending on preparation method or crystal system, but aluminium phosphate is known to show a weak solid acidity as +1.5 to +4.8 in Hammett acidity function HO (Kiyoko Sakamoto, et al., NIKKASHI, 1995 (9), p 681-688).

In the production method for acrolein, acrolein is formed by a gas phase dehydration reaction where a reaction gas containing glycerin gas and a catalyst are brought into contact in a reactor optionally selected from, for example, fixed-bed reactor, fluidized bed reactor, moving bed reactor, and the like. It should be noted that the production method for acrolein is not necessarily limited to the gas phase dehydration reaction where a reaction gas containing glycerin gas and a catalyst are brought into contact, but a liquid phase dehydration reaction where a glycerin solution and a catalyst are brought into contact can be applied. In the case of the latter, the liquid phase dehydration reaction can be implemented by conventionally known various methods such as a method where fixed-bed and distillation tower are combined, a method where mixing tank and distillation tower are combined, a method where a single stage of mixing tank is used, a method where multistage of mixing tanks are used, a method where multistage of distillation towers are used, and a method where these methods are combined. These methods may be any one of batch system or continuous system, but are usually implemented by a continuous system.

Hereinafter, a production method for acrolein by utilizing gas phase dehydration reaction which is superior in industrial productivity for acrolein will be explained as an example.

The reaction gas may be a gas composed of only glycerin or may contain a gas which is inert to the dehydration reaction of glycerin to adjust glycerin concentration in the reaction gas. Inert gas includes, for example, steam, nitrogen gas, carbon dioxide gas, air, or the like. Concentration of glycerin in the reaction gas is usually 0.1 to 100% by mole, preferably 1% by mole or more, and more preferably 5% by mole or more to conduct the production of acrolein economically and in high efficiency.

Since the catalyst of the present invention is a catalyst for glycerin dehydration having a high selectivity for acrolein, acrolein can be obtained in high yield even when flow rate of the reaction gas is set at a high level. Flow rate of the reaction gas, when represented in space velocity of gas per unit volume of catalyst (GHSV), is usually 50 to 20000 hr$^{-1}$, preferably 10000 hr$^{-1}$ or less, and more preferably 4000 hr$^{-1}$ or less to conduct the production of acrolein economically and in high efficiency.

Reaction temperature is usually 200 to 500° C., preferably 250 to 450° C., and more preferably 300 to 400° C.

Pressure of the reaction gas is not particularly limited so long as the pressure is in a range of pressure where glycerin does not condense, but usually 0.001 to 1 MPa, preferably 0.01 to 0.5 MPa, and more preferably 0.3 MPa or less.

When dehydration reaction of glycerin is carried out continuously, sometimes a carbon-like substance adheres on the surface of the catalyst resulting in decrease in catalytic activity. In particular, selectivity for acrolein decreases and selectivity for propionaldehyde increases. In such case, by subjecting the catalyst to regeneration treatment where the catalyst and a regeneration gas are brought into contact, the carbon-like substance adhered on the surface of the catalyst can be removed and catalytic activity can be recovered. The regeneration gas includes, for example, an oxidative gas such as oxygen and air containing oxygen. The regeneration gas may contain an inert gas to the regeneration treatment such as nitrogen, carbon dioxide and steam, if necessary. When a rapid heat generation is predicted by a contact of the catalyst and oxygen, it is recommended to contain an inert gas in the regeneration gas to suppress the rapid heat generation. Temperature of the regeneration treatment is not particularly limited, so long as the carbon-like substance can be removed at the temperature without the catalyst being thermally-deteriorated, but the temperature is preferably the burning temperature or lower in production of the catalyst.

Crude acrolein obtained by the dehydration reaction of glycerin contains by-products. Therefore, preferably the resultant crude acrolein is purified. By-products include, besides propionaldehyde, for example, phenol, 1-hydroxyacetone, allylalcohol, and the like. When the crude acrolein is purified, mainly phenol and/or 1-hydroxyacetone are removed. By removing these by-products, yield of acrylic acid is improved when acrylic acid is produced from acrolein. In particular, by removing 1-hydroxyacetone, amount of acetic acid to be generated can be reduced.

In view of improvement in yield of acrylic acid, it is considered preferable to increase an amount of phenol and/or 1-hydroxyacetone to be removed. Therefore, both of mass ratio Ph/A of acrolein (A) and phenol (Ph) after purification and mass ratio H/A of acrolein (A) and 1-hydroxyacetone (H) after purification are preferably 0.020 or less, more preferably 0.010 or less, and further more preferably 0.005 or less. However, when an amount of phenol and/or 1-hydroxyacetone to be removed is increased, sometimes loss of acrolein increases or purification of acrolein becomes cumbersome. In view of this situation, mass ratio Ph/A and mass ratio H/A are preferably $1\times10^{-9}$ or more, more preferably $1\times10^{-7}$ or more, and further more preferably $1\times10^{-5}$ or more.

Boiling points of acrolein, phenol and 1-hydroxyacetone are about 53° C., about 182° C. and about 146° C., respectively. By utilizing these differences in boiling points, phenol and/or 1-hydeoxyacetone can be removed from the crude acrolein. Such method includes, for example, a method where the crude acrolein in a liquid state is treated in a distillation tower to fractionally distill acrolein having a lower boiling point than those of the substances to be removed; a method where the crude acrolein in a gas state is treated in a condensation tower to condense the substances to be removed having a higher boiling points than that of acrolein; a method where a gas is blown into the crude acrolein introduced into an evaporation tower to vaporize acrolein having a lower boiling point than those of the substances to be removed; and the like.

In addition, melting points of acrolein, phenol and 1-hydroxyacetone are about −87° C., about 43° C. and about −17° C., respectively. By utilizing these differences in melting points, phenol and/or 1-hydeoxyacetone can be removed from the crude acrolein. The method includes, for example, a method where the crude acrolein is cooled to remove deposits of phenol and/or 1-hydroxyacetone, and the like.

It should be noted that boiling point and melting point of propionaldehyde are about 48° C. and about −81° C., respectively, and propionaldehyde can be removed from the crude acrolein by utilizing a difference in boiling point or melting point from those of acrolein. However, since either difference in boiling point or melting point from those of acrolein is small, loss of acrolein may be increased. For this reason, propionaldehyde generated in the dehydration reaction is preferably used accompanying to acrolein which is a raw material of acrylic acid without removing from acrolein.

<Production Method for Acrylic Acid by Oxidation of Acrolein>

Acrylic acid can be produced by oxidizing acrolein which is obtained by the above-described production method for acrolein.

When glycerin derived from biodiesel is used as a raw material in the present invention, the resultant crude acrolein may be used for producing acrylic acid without purifying. However, the resultant crude acrolein contains phenol, 1-hydroxyacetone, methoxyacetone, 3-methoxypropanal, and the like as by-products, and these by-products could cause decrease in catalytic activity and decrease in yield, or could cause contamination of by-products such as formic acid, acetic acid, propionic acid, pyruvic acid and 3-methoxypropionic acid in acrylic acid. Therefore, the crude acrolein may be used after purification. When purification is carried out, purification can be conducted by a conventionally known method, and a method where a collection liquid obtained by using condensed liquid of reaction composition and collection solvent is distilled, and a method using a purification equipment provided with collection tower and stripping tower described in JP-A-2008-115103 are exemplified. When the crude acrolein is not purified, impurities in acrylic acid may be removed by purifying acrylic acid in a post-step. Preferably the crude acrolein is used without purification from the viewpoint that process is simplified and production cost can be reduced.

Acrylic acid is produced preferably by co-existing a gas containing acrolein (hereinafter, sometimes referred to as "acrolein-containing gas") and a catalyst to oxidize acrolein (hereinafter, sometimes referred to as "catalyst for acrolein oxidation") into an oxidation reactor optionally selected from fixed-bed reactor, moving bed reactor, fluidized bed reactor, and the like, and subjecting acrolein to gas phase oxidation at a temperature of 200 to 400° C. It should be noted that propionic acid is formed from propionaldehyde accompanied by oxidation of acrolein.

The catalyst for acrolein oxidation is not particularly limited, so long as the catalyst is the conventionally known catalyst for acrolein oxidation to be used when acrylic acid is produced by catalytic gas phase oxidation of acrolein using molecular oxygen or a gas containing molecular oxygen. The catalyst for acrolein oxidation includes, for example, a mixture of metal oxides or complex oxide of iron oxide, molybdenum oxide, titanium oxide, vanadium oxide, tungsten oxide, antimony oxide, tin oxide, copper oxide, and the like. Among these catalysts, molybdenum-vanadium type catalyst containing molybdenum and vanadium as main components is particularly preferable. In addition, the catalyst for acrolein oxidation may be a supported type catalyst where a mixture of metal oxides or complex oxide as described above is supported on a carrier (for example, inorganic oxide such as of silica, alumina and zirconia, or complex oxide thereof, inorganic substance such as silicon carbide).

As for an amount of oxygen to be added to the acrolein-containing gas used for production of acrylic acid, an upper limit thereof should be appropriately set, because excessive addition of oxygen may cause combustion of acrolein accompanied by a risk of explosion.

By gas phase oxidation reaction of acrolein, a gaseous material containing crude acrylic acid can be obtained. In the collection step, this gaseous material can be liquefied by condensing by cooling or solvent collection to obtain a crude acrylic acid solution. This crude acrylic acid solution can be supplied to the crystallization step of the present invention.

Next, production method for acrylic acid by utilizing biomass and the like which are renewable resources will be shown. Though a direct route from the biomass to acrylic acid does not exist, acrylic acid can be prepared comparatively easily by decomposing lactic acid (hereinafter, also referred to as 2-hydroxypropionic acid, 2HP), cellulose, or the like which are natural products and easily available to obtain saccharides, further fermenting the saccharides to prepare hydroxycarboxylic acid such as 3-hydroxypropionic acid (hereinafter, also referred to as 3HP), and dehydrating hydroxycarboxylic acid. Acrylic acid can be obtained also by dehydrating a hydroxycarboxylate salt.

<Production Method for Hydroxypropionic Acid>

Hydroxycarboxylic acid and/or a salt thereof can be obtained from various sources. As a carbon source, recyclable organism-derived resources are suitably used from the viewpoint of global warming and environmental protection. 2-Hydroxypropionic acid from natural product, or 2-hydroxypropionic acid or 3-hydroxypropionic acid which is prepared by obtaining a saccharide by decomposing 2-hydroxypropionic acid, cellulose, or the like obtained, and further fermenting the saccharide can be used.

A 2-hydroxypropionic acid aqueous solution can be obtained by a known method, for example, by a fermentation using lactic bacteria described in Advances in Applied Microbiology, Vol. 42, p. 45-95 (1996) and a fermentation using a fungi (*Rhizopus oryzae*) described in Enzyme and Microbial Technology, Vol. 26, p. 87-107 (2000).

A 3-hydroxypropionic acid aqueous solution can also be obtained by a known method, for example, by fermentation using *E. coli* transgenic for *Streptomyces griseous* ATCC 21897-derived β-alanine aminotransferase and using glucose as a carbon source described in WO 2008/027742, and also by fermentation using *E. coli* transgenic for *Klebsiella pneumonia*-derived glycerin dehydratase and *E. coli*-derived aldehyde oxidase and glycerin as a carbon source described in WO 2001/016346. The above-described literature was described as an example of getting an aqueous 3-hydroxypropionic acid, but a bacterium or a recombinant bacterium to be used for fermentation is not particularly limited, so long as the method of the present invention is used, and a 3-hydroxypropionic acid aqueous solution obtained by the fermentation using a living organism having a 3-hydroxypropionic acid formation potential can be utilized in the method according to the present invention. In addition, besides fermentation, even a 3-hydroxypropionic acid aqueous solution obtained by contacting a saccharide as a raw material and a living organism can be converted to acrylic acid by the method according to the present invention. "Contacting saccharide and living organism" includes carrying out a reaction using a microorganism or processed material thereof in the presence of saccharide to be utilized as a raw material. Said processed material includes fungus body treated with acetone, toluene, or the like, dead fungus body, lyophilized fungus body, crushed fungus body, cell-free extract from crushed fungus body, crude enzyme liquid extracted therefrom, purified enzyme, and the like. In addition, a 3-hydroxypropionic acid aqueous solution obtained by reacting using fungus body, said processed materials, enzymes, or the like immobilized on a carrier by common method can also be used.

<Production Method for Acrylic Acid by Dehydration of Hydroxypropionic Acid>

To obtain the crude acrylic acid by dehydrating hydroxypropionic acid, a known method can be employed. For example, JP-A-2005-521718 describes a method where an unsaturated carboxylic acid or a salt thereof is produced by preparing an aqueous solution or a solution containing 2- or 3-hydroxycarboxylic acid (2HP and 3HP) obtained by fermentation or the like or a salt thereof, subjecting the solution to dehydration by heating in the presence or absence of a dehydration catalyst. WO 2005/095320 describes a method where 2- or 3-unsaturated carboxylic acid is prepared by introducing an aqueous solution containing 2- or 3-hydroxycarboxylic acid into a reactor where an inert ceramics or the like and an acidic or basic solid catalyst are maintained and then heating. WO 2007/106100 describes a method where a material containing 3-hydroxycarbonyl compound substantially in a liquid form is introduced into a reactor, and converting in the reactor to obtain a reaction product containing 2- or 3-unsaturated carboxylic acid compound. In this case, an acidic catalyst, a basic catalyst, or the like is used in the reactor.

The thus obtained acrylic acid is obtained as a liquid form material or a gaseous form material containing crude acrylic acid. The liquid form material can be used in the present invention as a crude acrylic acid solution as it is. The gaseous form material can be converted to a crude acrylic acid solution by liquefying using cooling and condensing, collection by solvent, or the like, and this crude acrylic acid solution can be used for the crystallization method of the present invention.

Subsequently, the third aspect and the fourth aspect of the present invention will be explained.

The third aspect of the present invention is a method for producing a hydrophilic resin, comprising polymerizing monomers containing acrylic acid obtained by the crystallization method according to the first aspect of the present invention or a product acrylic acid obtained by the adjustment method according to the second aspect of the present invention.

In addition, the forth aspect of the present invention is a method for producing a water-absorbing resin, comprising polymerizing monomers containing acrylic acid obtained by the crystallization method according to the first aspect of the present invention or a product acrylic acid obtained by the adjustment method according to the second aspect of the present invention.

Since acrylic acid produced by the method of the present invention has a stable quality, when used as a monomer for producing a hydrophilic resin such as water-absorbing resin and water-soluble resin, control of polymerization reaction becomes easy, resulting in stable quality of a hydrophilic resin, and various properties such as absorption performance and dispersibility of inorganic materials are improved. In particular, since acrylic acid produced by the method of the present invention is extremely useful as a raw material to produce a water-absorbing resin which has high water-absorbing performance and high quality, because it has a stable quality and polymerization reaction can be easily controlled.

Hereinafter, definitions relating to the water-absorbing resin of the present invention, as well as suitable embodiments for production will be explained.

(1) "Water-Absorbing Resin"

"Water-absorbing resin" in the present invention means a water-swellable and water-insoluble polymer gelling agent. It should be noted that "water-swellable" means that CRC (Centrifuge Retention Capacity) specified in ERT 441.2-02 is usually 5 [g/g] or more. Also, "water-insoluble" means that Ext (content of water-soluble component) specified in ERT 470.2-02 is usually 0 to 50% by weight.

The above-described water-absorbing resin can be appropriately designed corresponding to use thereof and is not particularly limited, but a hydrophilic cross-linked polymer which is obtained by cross-linking polymerization of unsaturated monomer having a carboxyl group is preferable. In addition, the water-absorbing resin is not limited to a form where a total amount (100% by weight) consists of the polymer, but may contain an additive and the like within a range where the above-described performance is maintained.

In the present invention, the water-absorbing resin means a water-absorbing resin which arbitrarily contains a graft component, and comprises mainly acrylic acid and/or a salt thereof (hereinafter, referred to as "acrylic acid (salt)" as a repeating unit. Specifically, the water-absorbing resin means a polymer which comprises usually 50 to 100% by mole of acrylic acid (salt) in the all of monomers (excluding cross-linking agent) used for the polymer, and the water-absorbing resin comprises preferably 70 to 100% by mole, more preferably 90 to 100% by mole, and particularly preferably substantially 100% by mole of acrylic acid (salt).

(2) "EDANA" and "ERT"

"EDANA" is an abbreviated name of European Disposables and Nonwovens Associations, and "ERT" is an abbreviated name of the measurement method for water-absorbing resin (EDANA Recommended Test Method) which is the European standard (nearly the world standard). It should be noted that in the present invention, properties of a water-absorbing resin are measured according to the original text of ERT (known literature: revised in 2002), unless otherwise noted.

(a) "CRC" (ERT 441.2-02)

"CRC" is an abbreviated name of Centrifuge Retention Capacity, and means water absorption ratio under no pressure (hereinafter, sometimes referred to as "water absorption ratio"). Specifically, CRC is a water absorption ratio (unit: [g/g]) after free swelling in a 0.9% by weight sodium chloride aqueous solution for 30 minutes and further draining by a centrifugal separator.

CRC of the water-absorbing resin obtained by the present invention is said to be 20 to 100 g/g, preferably 25 to 50 g/g, and more preferably 27 to 45 g/g.

(b) "AAP" (ERT 442.2-02)

"AAP" is an abbreviated name of Absorption Against Pressure, and means water absorption ratio under pressure. Specifically, AAP is a water absorption ratio (unit: [g/g]) after swelling in a 0.9% by weight sodium chloride aqueous solution for 1 hour under a load of 2.06 kPa, but in the present invention, for 1 hour under a load of 4.83 kPa.

AAP of the water-absorbing resin obtained by the present invention is said to be 20 to 30 g/g, and preferably 22 to 30 g/g.

(c) "Ext" (ERT 470.2-02)

"Ext" is an abbreviated name of Extractables, and means content of water-soluble component (amount of water-soluble component). Specifically, Ext is a value (unit: % by weight) obtained by stirring a mixture of a water-absorbing resin (1 g) in a 0.9% by weight sodium chloride aqueous solution (200 g) at 500 rpm for 16 hours, and then measuring an amount of dissolved polymer by pH titration. Ext of the water-absorbing resin obtained by the present invention is said to be 0 to 30 g/g, and preferably 0 to 20 g/g.

(d) "FSC" (ERT 440.2-02)

"FSC" is an abbreviated name of Free Swell Capacity, and means free swelling ratio. Specifically, FSC is a water absorption ratio (unit: [g/g]) obtained by dipping a water-absorbing resin (0.20 g) in a 0.9% by weight sodium chloride aqueous solution for 30 minutes, and then measuring without carrying out the draining by a centrifugal separator.

(e) "Residual Monomers" (ERT 410.2-02)

"Residual Monomers (RM)" means an amount of monomers remaining in a water-absorbing resin. Specifically, RM is a value (unit: ppm) obtained by adding a water-absorbing resin (1.0 g) into a 0.9% by weight sodium chloride aqueous solution (200 cm$^3$), stirring the mixture at 500 rpm for 1 hour, and measuring an amount of monomer eluted into said aqueous solution by a high performance liquid chromatography. RM of the water-absorbing resin obtained by the present invention is said to be 1000 ppm or less, and preferably 500 ppm or less.

(f) "PSD" (ERT 420.2-02)

"PSD" is an abbreviated name of Particle Size Distribution, and means particle size distribution measured by a sieve classification. It should be noted that weight average particle size (D 50) and particle size distribution width are measured by the same method as in "(1) Average Particle Diameter and Distribution of Particle Diameter" described in EP-A-0349240, page 7, line 25-43.

(3) "Liquid Permeability"

"Liquid permeability" means flow of a liquid flowing between particles of swollen gel under loaded or unloaded condition. Representative measurement method for this fluid permeability includes SFC (Saline Flow Conductivity) and GBP (Gel Bed Permeability).

"SFC (Saline Flow Conductivity) means liquid permeability of 0.69% by weight saline against a water-absorbing resin under 0.3 psi of loading. SFC is measured according to the SFC test method described in U.S. Pat. No. 5,669,893. Unit is (cm$^3$ s 10$^{-7}$/g).

"GBP" means liquid permeability of 0.69% by weight saline against a water-absorbing resin under loaded condition or free expansion. GBP is measured according to the GBP test method described in a pamphlet of WO 2005/016393.

SFC of the water-absorbing resin obtained by the present invention is said to be 1 or more, and preferably 5 or more.

(4) Embodiments Suitable for Production

A water-absorbing resin can be obtained by using acrylic acid and/or a salt thereof produced by the method of the present invention as a main component of monomers, cross-linking polymerization using a cross-linking agent of around 0.01% by mole or more and 5% by mole or less and a radical polymerization initiator of around 0.001% by mole or more and 2% by mole or less to acrylic acid and/or a salt thereof, and then drying and crushing.

Preferred production methods of a water-absorbing resin in the viewpoint of improved productivity include those described in, for example, U.S. Pat. No. 6,867,269, U.S. Pat.

No. 6,906,159, U.S. Pat. No. 7,091,253, the pamphlet of WO 01/038402, and the pamphlet of WO 2006/034806.

In particular, as a polymerization method for acrylic acid obtained by the method of the present invention, for example, continuous belt polymerization (disclosed in U.S. Pat. No. 4,893,999, U.S. Pat. No. 6,241,928, US-A-2005/215734), continuous kneader polymerization, batch kneader polymerization (disclosed in U.S. Pat. No. 6,987,151, U.S. Pat. No. 6,710,141, and the like) are preferably applied, but not particularly limited thereto.

The polymer obtained by the aforementioned methods is preferably converted to a granular water-absorbing resin by the production methods disclosed in U.S. Pat. No. 4,920,202, U.S. Pat. No. 5,264,495, U.S. Pat. No. 5,275,773, U.S. Pat. No. 6,207,796, U.S. Pat. No. 6,164,455, U.S. Pat. No. 6,207,796, U.S. Pat. No. 6,291,636, U.S. Pat. No. 6,875,511, and the like.

Furthermore, depending on purpose or use of the water-absorbing resin, in particular, when the water-absorbing resin is used for hygiene material, the water-absorbing resin is preferably subjected to surface cross-linking. As a specific embodiment, the production methods disclosed in EP-B-0349240, EP-B-0605150, EP-B-0450923, EP-B-0812873, EP-B-0450924, EP-B-0668080, JP-A-7-242709, JP-A-7-224304, U.S. Pat. No. 5,409,771, U.S. Pat. No. 5,597,873, U.S. Pat. No. 5,385,983, U.S. Pat. No. 5,610,220, U.S. Pat. No. 5,633,316, U.S. Pat. No. 5,674,633, U.S. Pat. No. 5,462,972, WO 99/42494, WO 99/43720, WO 99/42496, and the like, are preferable.

It should be noted that the above-described literatures have been incorporated herein by reference.

EXAMPLES

Hereinafter, the present invention will be explained more specifically by means of Examples.

Example 1

A reaction gas was obtained by catalytic gas phase oxidation reaction of propylene by the same method as in Example 1 in JP-A-2005-15478, and said reaction gas was brought into contact with an aqueous solution for collection, to obtain an acrylic acid solution having a composition of acrylic acid (90.0% by mass), water (3.2% by mass), acetic acid (1.9% by mass), maleic acid (0.6% by mass), acrylic acid dimer (1.5% by mass), furfural (0.07% by mass), benzaldehyde (0.27% by mass), formaldehyde (0.06% by mass), hydroquinone (0.1% by mass), and other impurities (2.3% by mass) from the bottom of the collection tower. It should be noted that a temperature of the bottom of the collection tower in this time, that is, a temperature of the acrylic acid solution taken out from the collection tower was 91° C.

Next, this acrylic acid solution was, after cooled down to around the external temperature, fed into a crystallizer, and was purified by repeating a dynamic crystallization 4 times. This dynamic crystallization was carried out in a crystallizer according to the crystallizer described in JP-B-53-41637. That is, the crystallizer is the one where a reservoir (collector section) has been provided in the lower part, a liquid in the reservoir is transferred to the upper part of the tube through a metal tube having a length of 6 m and a internal diameter of 70 mm, and the liquid is flowed down on the internal wall surface in a form of falling film. The surface of tube has been constituted with double-jacket, which is controlled so as to become a constant temperature by a thermostat. The first time of dynamic crystallization was carried out by the following procedures.

1. Crystallization:

An acrylic acid solution was fed to a reservoir, and flowed down on the surface of tube wall (the inner surface of the crystallization tube) in a form of falling film using a circulation pump, and temperature of the jacket was decreased to the freezing point or lower, to crystallize about 60 to 90% by mass of the acrylic acid solution on the wall surface (the inner surface of the crystallization tube).

2. Sweating:

Circulation pump was stopped, and a temperature of the jacket was raised to near the freezing point until about 2 to 5% of the acrylic acid crystal was sweated. After the sweating, the remaining molten liquid were pumped out.

3. Melting:

Temperature of the jacket was raised to the freezing point or higher to melt the crystal, which was pumped out. After initiation of the melting, the molten liquid melted was circulated to the upper part of the equipment, and flowed down on the acrylic acid crystal.

The molten liquid obtained by the above-described first dynamic crystallization was subjected to crystallization, sweating and melting again as the second to the fourth dynamic crystallizations, in the same way as described above except that the above-described molten liquid was introduced instead of the acrylic acid solution.

In the melting step 3 of the above-described the third and the fourth dynamic crystallizations, a solution of 5% by mass p-methoxyphenol in acrylic acid was added into the bottom (collector section) of the crystallizer, after that the molten liquid melted from the crystallization tube was taken out from the bottom and circulated to the top of the crystallizer, and flowed down on the acrylic acid crystal.

Amount to be added of the solution of p-methoxyphenol in acrylic acid was 0.0133 kg/hour in average per hour. The circulated molten liquid was flowed down while wetting the acrylic acid crystal, to melt the acrylic acid crystal. Purified acrylic acid was obtained at 3.32 kg/hour. It should be noted that the solution of 5% by mass p-methoxyphenol in acrylic acid was added so that 200 ppm of p-methoxyphenol was contained in the purified acrylic acid.

Finally, the crystal taken out from the dynamic crystallizer was analyzed. It was found that purity of acrylic acid was 99.94% by mass, and the crystal contained water (92 ppm by mass), acetic acid (450 ppm by mass), maleic acid (2 ppm by mass), furfural (0.2 ppm by mass), benzaldehyde (0.1 ppm by mass), formaldehyde (0.0 ppm by mass), and acrylic acid dimer (41 ppm by mass). In addition, color tone of said acrylic acid was 2 (APHA).

Reference Example 1

Acrylic acid was produced by carrying out the same operations as in Example 1 except that melting of the acrylic acid crystal was carried out by adding a solution of 0.0995% by mass p-methoxyphenol in acrylic acid into the bottom of the crystallizer, circulating the solution to the top of the crystallizer and flowing down on the acrylic acid crystal, and falling down the circulated solution of p-methoxyphenol in acrylic acid and the molten liquid melted from the crystal while the acrylic acid crystal was wetted therewith. Amount to be added of the solution of p-methoxyphenol in acrylic acid was 0.83 kg/hour in average per hour. It should be noted that the solution of 0.0995% by mass p-methoxyphenol in acrylic acid had been warmed up at 37° C. before adding to the crystallizer. By this method, purified acrylic acid was obtained at 3.35 kg/hour.

Finally, the crystal taken out from the dynamic crystallizer was analyzed. It was found that purity of acrylic acid was 99.93% by mass, and the crystal contained water (110 ppm by mass), acetic acid (460 ppm by mass), maleic acid (2 ppm by mass), furfural (0.2 ppm by mass), benzaldehyde (0.1 ppm by mass), formaldehyde (0.0 ppm by mass), and acrylic acid dimer (103 ppm by mass). In addition, color tone of said acrylic acid was 7 (APHA).

Acrylic acid obtained by the method of Reference Example 1 showed that concentrations of water and acrylic acid dimer as well as color tone were more inferior compared with those in Example 1.

Example 2

Acrylic acid was produced by carrying out the same operations as in Example 1 except that p-methoxyphenol in a solid form was added into the bottom of the crystallizer (amount of p-methoxyphenol was adjusted so that 200 ppm of p-methoxyphenol was contained in the purified acrylic acid). Amount to be added of p-methoxyphenol was 0.000665 kg/hour in average per hour. By this method, purified acrylic acid was obtained at 3.31 kg/hour.

Finally, the crystal taken out from the dynamic crystallizer was analyzed. It was found that purity of acrylic acid was 99.94% by mass, and the crystal contained water (80 ppm by mass), acetic acid (450 ppm by mass), maleic acid (2 ppm by mass), furfural (0.2 ppm by mass), benzaldehyde (0.1 ppm by mass), formaldehyde (0.0 ppm by mass), and acrylic acid dimer (33 ppm by mass). In addition, color tone of said acrylic acid was 1 (APHA).

It should be noted that the present application is based on JP Application No. 2009-132000, and the disclosed contents have been incorporated herein in its entirety by reference.

EXPLANATION OF REFERENCE

1: Raw material of acrylic acid
3: Air
5: Dilution gas
10 Catalytic gas phase oxidation catalyst
20 Reactor
25 Acrylic acid containing gas
30 Acrylic acid collection tower
31 Acrolein separation tower
32 Discharging gas from the top of collection tower
33 Aqueous solution for collection
33' Water for collection
34 Recycle gas
35, 35' Acrylic acid containing solution
36 Cooling tower
39 Cooler
50, 81 Crystallizer (batch system dynamic crystallizer)
53 Pre-purification separation equipment
60 Product acrylic acid
70 Distillation tower
71 Distillate
73 Thin film evaporator
75 Thermal decomposition tank
82, 83, 85, 86 Line
84 Crystallization tube
87, 89 Pump
88 Tank
100 Collector section

The invention claimed is:

1. A method for crystallizing (meth) acrylic acid comprising the steps of: (1) crystallization operation, (2) sweating operation and (3) melting operation,
    wherein
    (1) the crystallization operation comprises depositing an (meth)acrylic acid crystal,
    (2) the sweating operation comprises sweating the (meth) acrylic acid crystal to obtain an (meth)acrylic acid crystal containing a reduced amount of impurities, and
    (3) the melting operation comprises melting a part of the (meth)acrylic acid crystal containing a reduced amount of impurities to obtain a molten liquid melted after initiation of the melting and,
    wherein
    (a) a polymerization inhibitor is added to the molten liquid melted after initiation of the melting and
    (b) the molten liquid containing the polymerization inhibitor is circulated and fed to the (meth)acrylic acid crystal containing a reduced amount of impurities until all of the (meth)acrylic acid crystal is melt.

2. The method for crystallizing (meth)acrylic acid according to claim 1, wherein a solid or a concentrated solution of the polymerization inhibitor is added the molten liquid melted after initiation of the melting.

3. The method for crystallizing (meth)acrylic acid according to claim 1, wherein the (meth)acrylic acid crystal is obtained by crystallizing a crude (meth)acrylic acid using a dynamic crystallizer.

4. The method for crystallizing (meth)acrylic acid according to claim 1, wherein the (meth)acrylic acid crystal is obtained by crystallizing a crude (meth)acrylic acid using a melt crystallizer, and the polymerization inhibitor is added directly to the crystalline molten liquid of a collector section of said crystallizer.

5. The method for crystallizing (meth)acrylic acid according to claim 1, wherein the (meth)acrylic acid to be provided to the crystallization method is obtained by:
    a production method comprising a step where at least one kind of raw material of (meth)acrylic acid selected from the group consisting of alkane, alkene, alkanol and alkanal, each having 3 to 4 carbon atoms, is subjected to a catalytic gas phase oxidation;
    a production method comprising a step where glycerin or 2-methylglycerin is dehydrated to be converted to (meth)acrolein, and a step where said (meth)acrolein is further oxidized to be converted to (meth)acrylic acid; or
    a production method comprising a dehydration step where hydroxypropionic acid or 2-methyl-3-hydroxypropionic acid is converted to (meth)acrylic acid.

6. The method for crystallizing (meth)acrylic acid according to claim 2, wherein the (meth)acrylic acid crystal is obtained by crystallizing a crude (meth)acrylic acid using a dynamic crystallizer.

7. The method for crystallizing (meth)acrylic acid according to claim 2, wherein the (meth)acrylic acid crystal is obtained by crystallizing a crude (meth)acrylic acid using a melt crystallizer, and the polymerization inhibitor is added directly to the collector section of said crystallizer.

8. The method for crystallizing (meth)acrylic acid according to claim 1, wherein the method is performed without installing an exclusive molten liquid tank or heating means for molten liquid at melting of the (meth)acrylic acid crystal.

* * * * *